(12) United States Patent
Hjørnevik et al.

(10) Patent No.: US 7,135,439 B2
(45) Date of Patent: Nov. 14, 2006

(54) FREE-FLOWING PRODUCTS COMPRISING POTASSIUM FORMATE

(75) Inventors: Leif Hjørnevik, Skien (NO); Ivar Johansen, Stathelle (NO)

(73) Assignee: Yara International ASA, Olso (NO)

( * ) Notice: Subject to any disclaimer, the term of this patent is extended or adjusted under 35 U.S.C. 154(b) by 247 days.

(21) Appl. No.: 10/468,862

(22) PCT Filed: Jan. 30, 2002

(86) PCT No.: PCT/NO02/00039

§ 371 (c)(1),
(2), (4) Date: Nov. 5, 2003

(87) PCT Pub. No.: WO02/066149

PCT Pub. Date: Aug. 29, 2002

(65) Prior Publication Data

US 2004/0091408 A1    May 13, 2004

(30) Foreign Application Priority Data

Feb. 23, 2001 (NO) .................................. 20010930

(51) Int. Cl.
*C09K 8/03* (2006.01)
(52) U.S. Cl. ........................ 507/103; 507/267; 562/609
(58) Field of Classification Search ................ 507/103, 507/267; 562/609
See application file for complete search history.

(56) References Cited

U.S. PATENT DOCUMENTS

| | | | | |
|---|---|---|---|---|
| 2,030,082 A | * | 2/1936 | Wiedbrauck et al. | ....... 423/428 |
| 3,801,511 A | * | 4/1974 | Lemoff | ....................... 510/276 |
| 5,804,535 A | | 9/1998 | Dobson et al. | |
| 6,017,856 A | | 1/2000 | Van Ooyen | |

FOREIGN PATENT DOCUMENTS

| | | |
|---|---|---|
| EP | 0572113 | 12/1993 |
| EP | 0 769 000 | 12/1999 |
| EP | 1 022 252 | 7/2000 |
| WO | 9742272 | 11/1997 |
| WO | WO98/08914 | * 3/1998 |

* cited by examiner

*Primary Examiner*—Philip C. Tucker
(74) *Attorney, Agent, or Firm*—Wenderoth, Lind & Ponack, L.L.P.

(57) ABSTRACT

The present invention relates to a free-flowing potassium formate product, containing 0.1–1 weight % water, and comprises 0.5–5 weight % of a water soluble anticaking agent selected among carbonates, chlorides and hydroxides of alkali metals, and having water affinity corresponding to less than equilibrium water relative humidity (Rh) of 16% at 22° C. The potassium formate is preferably crystalline potassium formate containing 1–2.5 weight % potassium carbonate and/or potassium hydroxide. The product may contain 1–2.5 weight % sucrose and/or manose as anticaking agents.

3 Claims, No Drawings

FREE-FLOWING PRODUCTS COMPRISING POTASSIUM FORMATE

This application is a 371 of PCT/NO02/00039, filed Jan. 30, 2002.

The present invention relates to free-flowing products comprising potassium formate as the main component.

Potassium formate as such is a rather novel industrial product. The solubility of K-formate in water is high, at 20° C. can stable solutions of up to 78 weight % potassium formate in water be established. Aqueous solutions of K-formate have recently found applications in water based drilling mud and completion fluid in the oil and gas industry, within de-icing of airport runways and as secondary coolant.

For the above applications it is often required that the K-formate is delivered as a dry, free-flowing product. Specially within the gas and oil industry this requirement has become important. The K-formate can be used to correct the concentration of potassium formate based mud and completion fluid, and under those circumstances it is also important that the K-formate dissolves rapidly and without dry residuals. However, due to its inherent properties, K-formate is normally difficult to handle and store as it easily picks up moisture resulting in caking of the product. The critical humidity of K-formate is approximately 15% relative humidity (Rh) at room temperature (22° C.), which equalizes a dew point of −5° C. in air. This implies that K-formate will absorb water under practically all environmental conditions and therefore has to be bagged in bags with water diffusional tight lining.

A further problem relates to the fact that unconditioned crystalline K-formate has a tendency in a very short time to create caking problems when stored, even at very low contents of water, i.e. less than 0.2%. For instance will a 25 kg bag of unconditioned K-formate become hard and stiff within 24 hours, and the process is enhanced if the bags are palleted and the bags are exposed to weight pressure.

The main object of the invention was to find a suitable anticaking agent that was compatible with the end use of K-formate and make the final product free-flowing.

Another object was to obtain a conditioned K-formate product that dissolved rapidly in water.

In order to function properly industrially, especially when applied in drilling and completion fluids, the conditioning agent for the K-formate product should meet the following requirements:

Said agent shall preferably have lower equilibrium humidity than potassium formate to be able to bind residual water in the latter.

The agent shall have a good anticaking effect.

The anticaking agent shall have a high water solubility.

The anticaking agent shall have a short dissolution time in concentrated potassium formate solutions.

The conditioning agent shall give no dramatical change to the desired pH-range of the liquid product (preferred pH 9–11).

The philosophy used by the inventors to find a suitable candidate that meets all these requirements, was to start with a screening of possible conditioning agents by measuring the equilibrium humidity created of each anticaking agent. This parameter expresses the agent's affinity for water, which is very important.

The problem with caking of a crystalline mass of K-formate is linked to the high affinity for water of this product. The water absorbed by the mass is found as a thin film around each particle, which creates a dissolution of product in the water film.

Crystalline bridges are therefore created between the particles which makes the mass sticky and hard, especially under weight pressure.

To counteract this mechanism addition of a component that has a higher affinity for water, i.e. lower equilibrium humidity than K-formate, should adsorb the water in the mass and create free flow between the K-formate crystalline particles.

The described mechanism is a well known effect of anticaking agents as silicates and starches which have a widespread use. The water solubility of these products is, however, very limited and the majority of them have not the correct affinity for water to act in a crystalline product of K-formate.

The first screening done by the inventors was to measure the equilibrium humidity of other possible agents. Those with a lower equilibrium humidity than K-formate should have a good chance to work.

Various tests were performed in order to test the working hypothesis and develop products that met the above defined requirements. The inventors then found that it was possible to obtain free-flowing K-formate products containing 0.1–1 weight % water provided that said product comprised 0.5–5 weight % of a water soluble anticaking agent selected among carbonates, chlorides and hydroxides of alkali metals, and having water affinity corresponding to less than equilibrium water relative humidity (Rh) of 16% at 22° C.

It was found that said product should preferably contain 1–2.5 weight % of said anticaking agent. Positive effect was detected already at 0.5 weight % of the anticaking agent, and the practical upper limit was found to be 5 weight %.

The most preferred anticaking agent proved to be potassium carbonate or potassium hydroxide.

Sucrose and/or manose in amounts of 1–2.5 weight % were also found to be useful anticaking agents for the above product.

The most preferred form of said product proved to be crystalline potassium formate containing potassium carbonate and/or potassium hydroxide as anticaking agent.

EXAMPLE 1

The chemical samples to be measured were allowed to temperate at room temperature for 1–2 days. 350 ml of a sample was placed in a 500 ml flask leaving 150 ml free air space above the sample. A Novasin relative humidity and temperature recorder was inserted through a hole in a rubber stopper which was inserted in the flask opening leaving an airtight system. The measuring tube of the recorder was now placed in the flask air zone above the product sample.

The flask and sample were left for 1 hour storage, and the equilibrium temperature and relative humidity were logged after 1 hour grace period.

The first screening of possible agents was done to find their equilibrium water partial pressure, which indicates their ability to absorb water. These data are presented in Table 1 showing equilibrium water partial pressures at room temperatures.

These agents were selected mainly by means of literature data describing their capability to lower water vapor pressure in mixtures with water, but also high solubility in water was used.

TABLE 1

| Component | Product test temperature ° C. | Relative humidity recorded % Rh | Equilibrium water partial pressure mbar |
|---|---|---|---|
| Potassium Formate | 23 | 16 | 4.6 |
| Lithium Carbonate | 23.4 | 43.5 | 12.4 |
| Lithium Bromide | 23.9 | 10.3 | 3.0 |
| Sodium Carbonate | 25.6 | 23.7 | 7.7 |
| Sodium Benzoate | 23.5 | 26.6 | 7.7 |
| Sodium Hydroxide | 23.6 | 10.2 | 2.9 |
| Disodium Phosphate*2 $H_2O$ | 23.7 | 23.2 | 6.7 |
| Potassium Carbonate | 24.0 | 10.3 | 3.0 |
| Potassium Bromide | 23.1 | 57.0 | 16.0 |
| Potassium Hydroxide | 23.6 | 10.2 | 2.9 |
| Potassium Thiocyanate | 24.8 | 44.5 | 13.8 |
| Potassium Acetate | 23.8 | 16.1 | 4.7 |
| Potassium/Sodium tatrate | 23.8 | 37.0 | 10.8 |
| Potassium Sorbate | 23.8 | 23.5 | 6.9 |
| Calcium Chloride*2 $H_2O$ | 23.3 | 11.3 | 3.2 |
| Magnesium Chloride*6 $H_2O$ | 23.9 | 10.4 | 3.1 |
| Zinc Chloride (anhydrous) | 22.8 | 10.3 | 2.8 |
| Zinc Sulphate*7 $H_2O$ | 23.9 | 63.7 | 18.7 |
| D(+) Glucose | 23.8 | 24.5 | 7.2 |
| D(+) Sucrose | 22.5 | 13.2 | 3.5 |
| D(+) Mannose | 23.1 | 17.4 | 4.9 |
| Silicate (Sipernate 22, Degussa) | 23.3 | 42.8 | 12.6 |
| Silicate (Sipernate 22S, Degussa) | 23.3 | 37 | 11 |
| Silicate (Sipernate 50 Degussa) | 23.9 | 46.7 | 13.7 |
| Silicate (GM1 Damolin) | 24.1 | 38.9 | 11.6 |
| Starch Caccava | 23.7 | 39.6 | 11.5 |
| Starch SP1 | 23.7 | 37.9 | 11.5 |

Water free potassium formate has an equilibrium relative humidity at 23° C. of 15%. The equilibrium relative humidity is increasing with increasing water content in the crystal mass, and at a water content of 0.5% the equilibrium relative humidity increases to 20%. This equalizes an equilibrium water vapor pressure range of 4.2–5.6 mbar.

The potassium formate crystalline product contained water in the range 0.2–0.5, and it was important that residual water in the product was absorbed by the anticaking agent to secure free flow of the formate particles.

The recorded data in Table 1 indicate the affinity for water of the agents. Preferably will an agent with a higher affinity for water (lower water partial pressure) than K-formate, bind/absorb the water and secure free flow of the main product.

Based on the fact that the K-formate product contained 0.2–0.5% water and had an equilibrium water partial pressure at 23° C. at 4.2–5.6 mbar, agents that had a lower water partial pressure and as such a higher water affinity, should theoretically work as anticaking agent in the formate product.

As can be seen from the results in Table 1 agents like potassium carbonate, potassium hydroxide, lithium bromide, calcium chloride magnesium chloride and sucrose should work according to the above hypothesis.

It also appears from Table 1 that well known anticaking agents as silicates and starches have too high equilibrium water vapor pressure to work as anticaking agents in potassium formate products mixes.

The requirement of high water solubility of the anticaking agent excludes components since most of them are insoluble or have a low solubility in water.

However, in order to find a suitable agent, the inventors had to check the most promising agents with regard to free flow and caking properties using well known test methods therefor.

EXAMPLE 2

For the free-flowing tests the inventors used glass laboratory silos with openings of 15.8 mm and 22 mm, respectively. The free-flowing ability is measured by recording the emptying time for 1 kg of potassium formate product mixed with the different anticaking agents in dosages of 1.5–3%.

Calcium formate, which is a non-hygroscopic free-flowing material was used as reference medium. Two parallel recordings were made for each sample. Table 2 below is presenting the average results.

TABLE 2

| Mixture | Flow time Opening 15.8 mm seconds | Flow time Opening 22 mm seconds |
|---|---|---|
| K-Formate, fresh dried and unconditioned | 16.7 ± 0.14 * | 6.90 ± 0.14 * |
| Calcium Formate, dry and unconditioned | 16.78 ± 0.52 | 7.15 ± 0.08 |
| K-Formate + 1.5% Lithium Bromide. | 12.36 ± 0.18 | 4.53 ± 0.06 |
| K-Formate + 3.0% Lithium Bromide | 11.18 ± 0.01 | 4.54 ± 0.04 |
| K-Formate + 1.5% Potassium Carbonate. | 12.22 ± 0.03 | 4.52 ± 0.05 |
| K-Formate + 3.0% Potassium Carbonate | 13.15 ± 0.04 | 4.88 ± 0.06 |
| K-Formate + 1.5% Potassium Hydroxide | 13.80 ± 0.05 | 6.82 ± 0.07 |
| K-Formate + 3.0% Potassium Hydroxide | 13.20 ± 0.04 | 4.87 ± 0.14 |
| K-Formate + 1.5% Potassium Acetate | No flow | No flow |
| K-Formate + 3.0% Potassium Acetate | 11.40 ± 0.10 | 4.78 ± 0.20 |
| K-Formate + 1.5% Pot./Sodium tatrate | 12.17 ± 0.06 | 4.61 ± 0.11 * |
| K-Formate + 3.0% Pot./Sodium tatrate | 12.36 ± 0.17 | 4.76 ± 0.02 |
| K-Formate + 1.5% Sodium Carbonate | 12.06 ± 0.01 | 5.00 ± 0.01 |
| K-Formate + 3.0% Sodium Carbonate | 11.90 ± 0.08 | 4.66 ± 0.01 |
| K-Formate + 1.5% DiSodium Phosphate | 12.13 ± 0.06 | 4.30 ± 0.07 * |
| K-Formate + 3.0% DiSodium Phosphate | 13.14 ± 0.07 | 4.67 ± 0.04 * |
| K-Formate + 1.5% Calcium Chloride | 11.75 ± 0.04 | 4.50 ± 0.01 |
| K-Formate + 3.0% Calcium Chloride | 12.36 ± 0.17 | 4.76 ± 0.02 |
| K-Formate + 1.5% Sipernate 22 | 14.27 ± 0.03 | 5.21 ± 0.02 |
| K-Formate + 3.0% Sipernate 22 | 15.06 ± 0.05 | 5.58 ± 0.02 |
| K-Formate + 1.5% Glucose | Flow impossible | Flow impossible |
| K-Formate + 3% Glucose | Flow impossible | Flow impossible |
| K-Formate + 1.5% Sucrose | 14.63 ± 1.52 * | 6.75 ± 0.354 |
| K-Formate + 3% Sucrose | 14.25 ± 1.20 * | 6.75 ± 0.495 |

* Need knocking on the silo to create flow.

It appeared from Table 2 that K-formate with low water content, freshly dried and unconditioned, had a low emptying time in the flow test compared to dry calcium formate, this caused by difference in particle size and shapes comparing the two products.

Table 2 also indicated that the most promising agents traced in Table 1 gave problem free flow characteristics for the product mixes in the silo tests. Agents that did not fulfil the requirements of lower equilibrium water pressure than 4.2–5.6 mbar gave problems in the flow tests (asterix *), except the mixtures with silicates.

To further develop the selection of a good anticaking agent the inventors carried out standard hardening tests for the crystal product mixed with the most promising agents detected in Table 2.

Some of the crystal product mixes in Table 2 that did not fulfil the vapor pressure requirement in Table 1, were included in the hardening tests to verify the hypothesis of the selection method.

EXAMPLE 3

Caking tests were carried out for the same mixtures as shown in Table 3.

Test samples (approx. 100 g) as presented in Table 3 were filled into small plastic bags with dimensions 10 cm×10 cm, and the opening was welded tight. The test bags are placed between 2 metal plates and a pressure of 3 bar was exposed to the upper plate. The pressure equalized a weight of 300 kg or approximately 1425 kg bags. The samples were left there for 3 days, 72 hours.

The weights were removed after 3 days.

The bags were now individually placed on a screen with 3.5 mm openings. The screen was placed above a weight which was weighing the powder released from the screen. The screen was connected to a pusher which is giving the screen a stroke, and the number of strokes necessary to empty the screen were recorded and logged on a computer.

The results are interpreted and classified in the following way:

No. of strokes <5: Risk of caking is unlikely or very low.
No. of strokes >5: Risk of caking is likely.

The probability of hardening or caking is increasing linearly with the number of strokes necessary above a number of 5.

The hardening number presented in the resulting curve is equal to the number of strokes necessary to break down the hardened material.

The samples were introduced to this test with 3 parallels.

The results are presented i Table 3 below which shows the heardening tests of K-formate samples with added anticaking agent (each test sample was investigated in 3 parallels):

TABLE 3

| Sample | Average hardening number | Hardening limit | Comment |
|---|---|---|---|
| K-Formate unconditioned | 24 | <5 | Caking |
| K-Formate, particulated, waterfree | 0 | <5 | No caking |
| Calcium Formate unconditioned | 0 | <5 | No caking |
| K-Formate + 1.5% Pot Carbonate | 0 | <5 | No caking |
| K-Formate + 3.0% Pot. Carbonate | 0 | <5 | No caking |
| K-Formate + 1.5% Pot. Hydroxide | 2.3 | <5 | No caking |
| K-Formate + 3.0% Pot. Hydroxide | 0 | <5 | No caking |
| K-Formate + 1.5% Pot. Acetate | 22.2 | <5 | Caking |
| K-Formate + 3.0% Pot. Acetate | 14.8 | <5 | Caking |
| K-Formate + 1.5% Lithium Bromide | 20.1 | <5 | Caking |
| K-Formate + 3.0% Lithium Bromide | 27.1 | <5 | Caking |
| K-Formate + 1.5% Sodium Carbonate | 55.5 | <5 | Caking |
| K-Formate + 3.0% Sodium Carbonate | 92.1 | <5 | Caking |
| K-Formate + 1.5% Disodium Phosphate | 50.5 | <5 | Caking |
| K-Formate + 3.0% Disodium Phosphate | 56.9 | <5 | Caking |
| K-Formate + 1.5% Sodium/Pot. tatrate | 46.6 | <5 | Caking |
| K-Formate + 3.0% Sodium/Pot. tatrate | 31.6 | <5 | Caking |
| K-Formate + 1.5% Calcium Chloride | 14.3 | <5 | Caking |
| K-Formate + 3.0% Calcium Chloride | 13.6 | <5 | Caking |
| K-Formate + 1.5% D-Glucose | 69.2 | <5 | Caking |
| K-Formate + 3.0% D-Glucose | 110.3 | <5 | |
| K-Formate + 1.5% D-Sucrose | 2.6 | <5 | No caking |
| K-Formate + 3.0% D-Sucrose | 1 | <5 | No caking |
| K-Formate + 1.5% Sipernate 22 | 86.4 | <5 | Caking |
| K-Formate + 3.0% Sipernate 22 | 67.0 | <5 | Caking |

It appears from Table 3 that calcium formate as a reference gave no caking as expected.

Also particulated water free K-formate (3 mm particles) which was based on a high temperature melting process, gave no caking. That result verifies that it is the residual water and the crystal bridge effect related to the residual water that creates the caking problem in the crystal mass.

The particulated water free K-formate did not cake during the test, but it picks up moisture very rapidly when exposed to the atmosphere, and then the particles will start caking. In order to avoid caking of this K-formate product it is essential that it is not exposed to moisture during storage and handling.

As can be seen from the results in Table 3, only potassium carbonate, sucrose and potassium hydroxide gave satisfying data in the hardening test. The two other agents tested with greater water affinity than potassium formate, that is lithium bromide and calcium chloride, gave too high hardening numbers and will only in special cases be applicable for preventing caking of K-formate.

Since crystalline K-formate is frequently used to upgrade K-formate based drilling and completion fluids in the oil & gas industry it was important to investigate the different product mixes' ability to form particle free solutions when used. The upgrading of K-formate based systems most often takes place in the Sp.gr. region 1.5–1.57 kg/l.

EXAMPLE 4

The ability of upgrading a water solution of K-formate with specific gravity (Sp.gr.) of 1.53 (71% potassium formate) to Sp.gr. 1.57 (75% potassium formate) by dry crystalline product to which there was added suitable anticaking candidates, was carried out by dissolution tests in the laboratory.

Results

The results are presented in Table 4 and show dissolution of conditioned K-formate products:

TABLE 4

| Dry Product | Sp. gr. before upgrade kg/l | Sp. gr. after upgrade kg/l | pH | Results |
|---|---|---|---|---|
| K-formate + 1.5% $K_2CO_3$ | 1.523 | 1.586 | 12.9 | Clear brine |
| K-formate + 1.5% LiBr | 1.523 | 1.587 | 11.6 | Clear brine |
| K-formate + 1.5% $CaCl_2$ | 1.523 | 1.584 | 11.5 | Precipitate |
| K-formate + 1.5% KOH | 1.523 | 1.585 | 15.4 | Clear brine |

TABLE 4-continued

| Dry Product | Sp. gr. before upgrade kg/l | Sp. gr. after upgrade kg/l | pH | Results |
|---|---|---|---|---|
| K-formate + 1.5% Sucrose | 1.523 | 1.58 | 10.5 | Precipitate |

As can be seen from Table 4, addition of dry K-formate containing calcium chloride and sucrose as anticaking agent to the K-formate solution results in precipitation, and accordingly this anticaking agent will not function in spite of its positive properties shown in Table 1. This will also happen with an anticaking agent based on chlorides of magnesium and zinc.

Though lithium bromide passed the dissolution test, the practical applicability is limited due to price and compatibility with the drilling and completion system.

The above example clearly demonstrates that the inventors have succeeded in arriving at conditioning and anticaking agents for K-formate making it free-flowing under practical storage and handling conditions. Though several possible agents passed the initial tests, surprisingly few proved to meet the requirements for practical use.

The invention claimed is:

1. Free-flowing potassium formate product comprising potassium formate particles, 0.1–1 weight % water, and 0.5–5 weight % of a water soluble anti-caking agent which is potassium carbonate and/or potassium hydroxide having a water affinity corresponding to less than equilibrium water relative humidity (Rh) of 16% at 22° C.

2. Free-flowing potassium formate product according to claim 1, wherein said product comprises 1–2.5 weight % potassium carbonate and/or potassium hydroxide.

3. Free-flowing potassium formate product according to claim 1, wherein the potassium formate particles are crystalline potassium formate particles.

* * * * *